(12) United States Patent
Decker et al.

(10) Patent No.: US 11,066,631 B2
(45) Date of Patent: Jul. 20, 2021

(54) PACK

(71) Applicant: XEBIOS DIAGNOSTICS GMBH, Duesseldorf (DE)

(72) Inventors: Ludwig Decker, Grevenbroich (DE); Christoph Mentzel, Burscheid (DE)

(73) Assignee: XEBIOS DIAGNOSTICS GMBH, Duesseldorf (DE)

(*) Notice: Subject to any disclaimer, the term of this patent is extended or adjusted under 35 U.S.C. 154(b) by 33 days.

(21) Appl. No.: 16/318,710

(22) PCT Filed: Jul. 14, 2017

(86) PCT No.: PCT/EP2017/067907
§ 371 (c)(1),
(2) Date: Jan. 18, 2019

(87) PCT Pub. No.: WO2018/015310
PCT Pub. Date: Jan. 25, 2018

(65) Prior Publication Data
US 2019/0218493 A1   Jul. 18, 2019

(30) Foreign Application Priority Data
Jul. 20, 2016 (DE) .................... 20 2016 004 498.3

(51) Int. Cl.
*C12M 3/00* (2006.01)
*C12M 1/00* (2006.01)
(Continued)

(52) U.S. Cl.
CPC ............. *C12M 23/10* (2013.01); *B65D 71/02* (2013.01); *B65D 77/00* (2013.01); *B65D 85/62* (2013.01); *C12M 23/46* (2013.01); *C12M 23/48* (2013.01); *C12M 99/00* (2013.01); *G01N 2035/0425* (2013.01)

(58) Field of Classification Search
None
See application file for complete search history.

(56) References Cited

U.S. PATENT DOCUMENTS 3,561,595 A * 2/1971 Weggeland ........ G11B 23/0236
206/757
3,712,463 A * 1/1973 Bestehorn .............. B65D 63/02
206/232

(Continued)

FOREIGN PATENT DOCUMENTS

CN  201817471 U  5/2011
DE  1720572 U  4/1956
(Continued)

OTHER PUBLICATIONS

English translation of DE 29622031 to Grunecker et al (generated 2020).*

(Continued)

*Primary Examiner* — Nathan A Bowers
(74) *Attorney, Agent, or Firm* — Norman B. Thot

(57) ABSTRACT

A pack includes at least one stack with Petri dishes which extends in a longitudinal direction, a connecting device which holds the at least one stack together, and an outer packaging which surrounds the at least one stack and which can be opened to remove the at least one stack.

11 Claims, 3 Drawing Sheets

(51) Int. Cl.
*B01L 1/00* (2006.01)
*C12M 1/22* (2006.01)
*B65D 71/02* (2006.01)
*B65D 77/00* (2006.01)
*B65D 85/62* (2006.01)
*G01N 35/04* (2006.01)

(56) References Cited

U.S. PATENT DOCUMENTS

| | | | | |
|---|---|---|---|---|
| 4,280,811 | A | * | 7/1981 | Howe, Jr. ............ B65D 33/001 493/386 |
| 4,828,110 | A | * | 5/1989 | Lems ................... B65D 71/02 206/150 |
| 5,388,687 | A | * | 2/1995 | Philip .................. B65B 27/083 100/34 |
| 5,718,157 | A | * | 2/1998 | Hawley ............. B65B 69/0025 241/605 |
| 5,855,853 | A | | 1/1999 | Zauser et al. |
| 5,863,496 | A | * | 1/1999 | McElhany ................ A61L 2/08 383/113 |
| 5,970,834 | A | * | 10/1999 | Garofano ............. B65B 43/145 29/426.3 |
| 6,193,067 | B1 | * | 2/2001 | McMahan .............. B65D 5/721 206/560 |
| 6,230,878 | B1 | * | 5/2001 | Lehr ........................ A45C 1/06 206/37 |
| 6,670,174 | B1 | * | 12/2003 | Smith ..................... C12M 23/10 435/303.2 |
| 7,273,750 | B1 | | 9/2007 | Olivier et al. |
| 2002/0043553 | A1 | * | 4/2002 | Man ..................... B65B 27/083 229/117.35 |
| 2005/0098473 | A1 | * | 5/2005 | Sheehan, Jr. ..... H01L 21/67369 206/710 |
| 2006/0099065 | A1 | * | 5/2006 | Neebe .................... B07C 3/008 414/800 |
| 2010/0035338 | A1 | | 2/2010 | Colin et al. |
| 2012/0261277 | A1 | | 10/2012 | Barnhizer |

FOREIGN PATENT DOCUMENTS

| | | |
|---|---|---|
| DE | 3218532 A1 | 11/1983 |
| DE | 691 05 317 T2 | 4/1995 |
| DE | 195 02 520 C1 | 3/1996 |
| DE | 296 22 031 U1 | 5/1998 |
| DE | 600 09 564 T2 | 3/2005 |
| EP | 0 087 031 A2 | 8/1983 |
| EP | 0 447 893 A2 | 9/1991 |
| EP | 1 953 219 A1 | 8/2008 |
| EP | 2 112 088 A1 | 10/2009 |
| EP | 2 803 590 A1 | 11/2014 |
| JP | 10059365 A * | 3/1998 |
| WO | WO 2012/145408 A2 | 10/2012 |

OTHER PUBLICATIONS

English abstract translation of JP 10-59365 to Nakaji et al (generated 2020).*

* cited by examiner

PACK

CROSS REFERENCE TO PRIOR APPLICATIONS

This application is a U.S. National Phase application under 35 U.S.C. § 371 of International Application No. PCT/EP2017/067907, filed on Jul. 14, 2017 and which claims benefit to German Patent Application No. 20 2016 004 498.3, filed on Jul. 20, 2016. The International Application was published in German on Jan. 25, 2018 as WO 2018/015310 A9 under PCT Article 21(2).

FIELD

The present invention relates to a pack of Petri dishes.

BACKGROUND

Petri dishes are flat, round, transparent dishes with lids that fit thereover. They are mostly used to cultivate microorganisms and for cell culture in biology or medicine. A generally flat layer of a usually gelatinous culture medium is created in the Petri dish for this purpose. The culture medium is usually produced on an agar base, sterilized in an autoclave by heating, and poured into the respective Petri dish while still warm and thus fluid therefor. It solidifies at room temperature and thus forms a so-called agar plate.

In clinical or industrial use, for example, a plurality of different Petri dishes provided with culture medium are often required in order to be able to qualify and quantify microorganisms in a series of experiments. Petri dishes with so-called "pre-poured culture media" are provided in packs of ten in tubular bags or in stocking films therefor. In order to use the individual Petri dishes, the tubular bags or the stocking films must be manually removed by the user. This requires a substantial amount of time, especially in the event of a larger requirement for Petri dishes.

SUMMARY

An aspect of the present invention is to provide a remedy therefor and a pack which reduces the time required for opening operations and which increases productivity, for example, of a laboratory.

In an embodiment, the present invention provides a pack which comprises at least one stack comprising Petri dishes which extends in a longitudinal direction, a connecting device configured to hold the at least one stack together, and an outer packaging which is configured to surround the at least one stack and which can be opened to remove the at least one stack.

BRIEF DESCRIPTION OF THE DRAWINGS

The present invention is described in greater detail below on the basis of embodiments and of the drawings in which.

DETAILED DESCRIPTION

Figure 1:
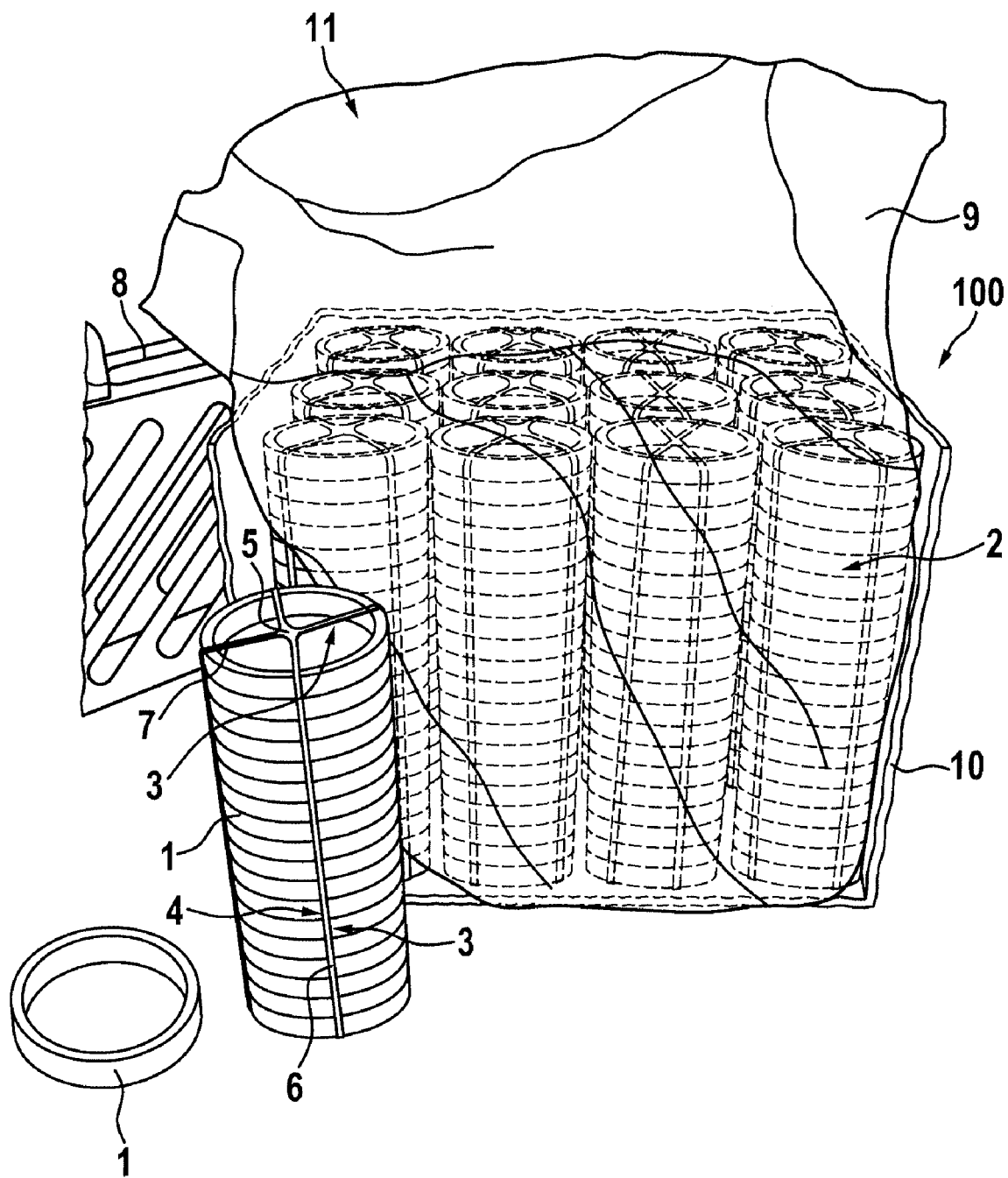
FIG. 1 shows a perspective view of an opened cardboard packaging having four rows of three stacks of Petri dishes each located in an outer packaging as well as a stack located in front thereof in the viewing direction, and a magazine located behind it in the viewing direction, which is partly covered by the cardboard packaging.
Figure 2:
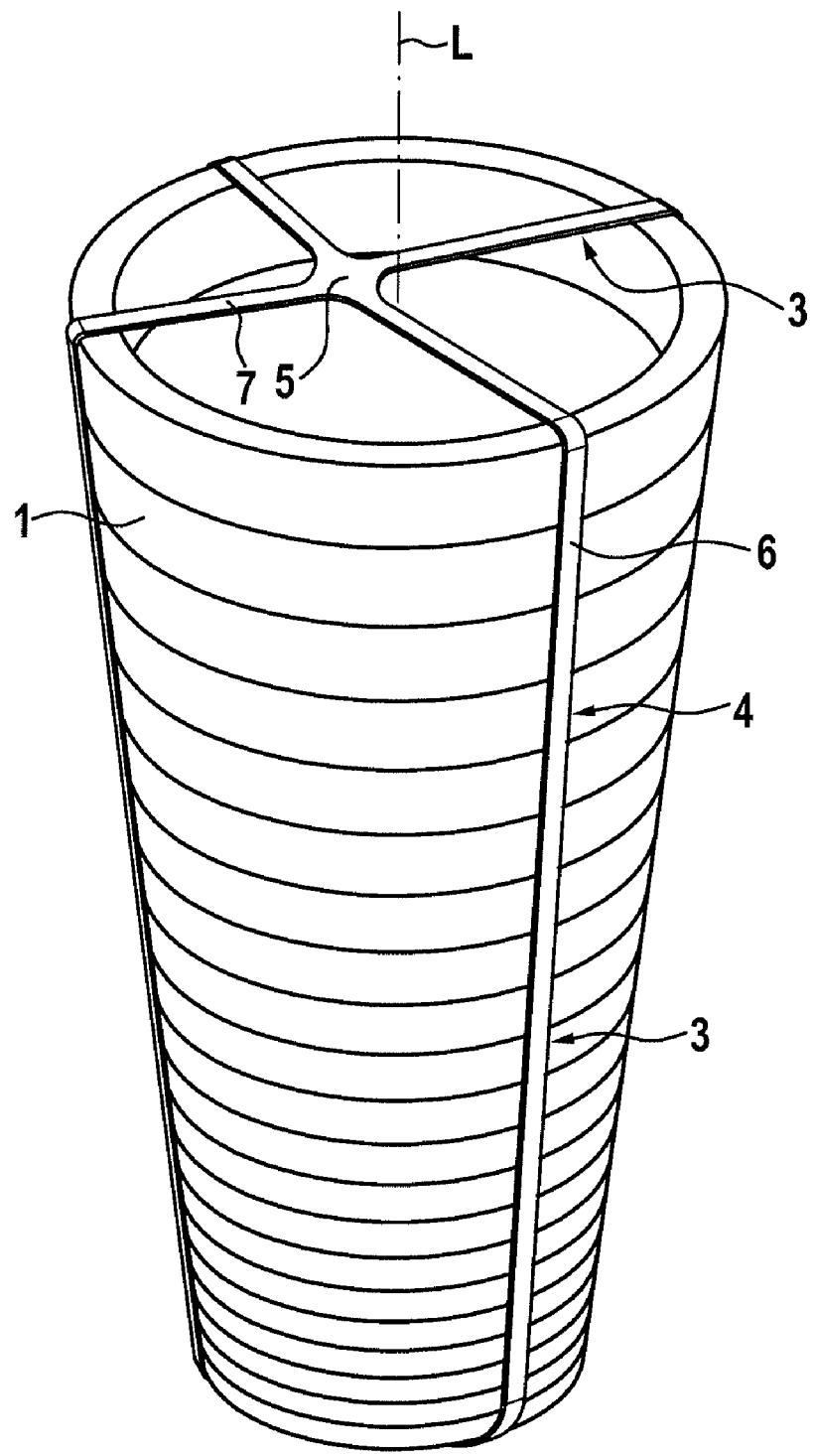
FIG. 2 shows a stack of Petri dishes held together with an exemplary embodiment of a connecting device in a perspective detail drawing.

The pack according to the present invention comprises at least one stack of Petri dishes extending in a longitudinal direction as well as a connection device which holds together the stack and which can, for example, be detachable via a severing process for removing Petri dishes from the stack. The connection device essentially has the task of holding together the stack of Petri dishes against an undesired falling apart, but does not have the function of shielding the stack from external influences, in particular, of keeping the Petri dishes sterile.

An outer packaging which surrounds the at least one stack of Petri dishes and which can be opened in order to remove the at least one stack serves to keep the Petri dishes sterile.

The allocation of the two different functionalities, i.e., "to keep the stack of Petri dishes together" and "to shield the Petri dishes against external influences, specifically to keep them sterile", to two different measures, namely, the detachable connecting device and the outer packaging that can be opened, has as a result that a stack of Petri dishes supplied sterile in the openable outer packaging can be removed shortly before further use, wherein the individual Petri dishes can, however, still be held together in the stack. The stack held together in this way can, for example, be supplied to a magazine of a device for laboratory automation without the danger arising of the stack falling apart or of the Petri dishes having to be individually inserted into the magazine. Once in the magazine, the connecting device can be released as needed, a process that can be configured to take place simply and quickly if the release is, for example, performed via a severing process.

It has been shown that the time requirement for loading a magazine of a device for laboratory automation with a stack of Petri dishes that have been provided in such a pack according to the present invention is significantly reduced as compared to the prior art.

In an embodiment of the present invention, the connecting device can, for example, have a strip material which at least partly surrounds the stack in its longitudinal direction. This strip material can be a strip of paper, cloth or film material, which is, for example, guided around the stack in the longitudinal direction so that it directly or indirectly touches the base of the one Petri dish that delimits one end of the stack and the lid of the other Petri dish that delimits the other end of the stack, wherein the strip forms an endless loop when both of its free ends are joined.

The strip material can, for example, be in the form of a banner wrap.

In an embodiment of the pack according to the present invention, the connecting device can, for example, comprise a strap arrangement made of an elastic, for example, a rubber-elastic material, that envelops the stack in its longitudinal direction. Because of the material properties of the elastic, for example, the rubber-elastic material, the strap arrangement can be easily placed around the stack and provides that individual Petri dishes of the stack are pressed against each other by the effect of the elastic force. With correspondingly higher extensibility of the strap arrangement, it is also possible to use a strap arrangement with a specific strap circumference in an unstressed state for different dimensional stacks, in particular for stacks of different lengths.

An especially reliable holding together of the Petri dishes forming a stack is achieved if the strap arrangement, for example, comprises two strap elements that cross each other and are connected to each other at two crossing points. If the crossing points in an approved assembly coincide somewhat with the longitudinal central axis of the stack, the stack is surrounded on its peripheral surface by strap strands spaced at about 90° from each other, which results in a particularly good holding together of the individual Petri dishes, which good holding is also not lost, for example, by turning over the stack of Petri dishes on a work surface or by otherwise clumsy handling. A stack of Petri dishes held together with a strap arrangement of this sort can be placed safely in a magazine of an analysis device or of a bioreactor without requiring special care. This can substantially reduce the time required for loading a magazine.

The holding together of the Petri dishes in a stack can be released in both embodiments by simply severing the strip material or the strap arrangement, for example, in the region of a crossing point, with, for example, a scalpel.

In an embodiment of the pack according to the present invention, the outer packaging can, for example, enclose a sterile interior volume in the unopened state. The at least one stack surrounded by an outer packaging can thereby be stored over a longer time span. It is thus possible to fill Petri dishes with culture medium in a device designed therefor, to put together stacks and provide the stacks with outer packagings in order to then provide the stacks to geographically remote users, such as laboratories, for example, via shipping services.

The outer packaging can comprise a film packaging.

The outer packaging can, for example, be designed to be torn open manually, whereby the time needed by the user to prepare the stacks of Petri dishes is additionally reduced.

It has been shown that it is particularly advantageous for handling if the at least one stack comprises between 45, particularly between 10 and 30, for example, approximately 20 Petri dishes, because this quantity of Petri dishes is easy to put together and keep together in a stack and because magazine sizes exist which can accept these quantities or portions thereof per stack. A quantity of Petri dishes per stack which, for example, corresponds to a quantity of Petri dishes which a magazine can accommodate in stack form can, for example, be provided. The stack held together by the connecting device can then be inserted into the magazine. Once in the magazine, the connecting device can then be severed, for example, using a cutting tool, if necessary, and the individual Petri dishes can be supplied individually for further use, for example, in the analysis device or in the bioreactor.

A pack according to the present invention can, for example, be provided in which the outer packaging includes between 2 and 20, for example, 6 or 12, stacks of Petri dishes, because this number of stacks is easy to handle and can usually be arranged in a symmetrical manner for the purpose of saving space.

Because of easy manageability, a pack can, for example, be provided in which either six stacks are arranged in the outer packaging in two rows of three stacks each or 12 stacks are arranged in four rows of three stacks each.

In particular if packs according to the present invention must be transported over greater distances between preparation and use, cardboard packaging can, for example, be provided that accommodates at least one outer packaging and at least partly surrounds it. The cardboard packaging can, for example, be designed to be opened and then closed again without damage in order to be able to reuse the cardboard packaging.

The cardboard packaging is designed so that it surrounds four rows of three stacks each, for example, about 10 or about 20 Petri dishes. Then either one outer packaging with four rows of three stacks each or two outer packagings, each with two rows of three stacks each, can be transported in a cardboard package.

In order to protect the stacks transported with one cardboard packaging from damage, an embodiment of a pack according to the present invention provides a dampening layer which can, for example, be provided between the bottom of the stacks and the cardboard packaging and, for example, between the top of the stacks and the cardboard packaging and which can, for example, comprise an air pillow.

The present invention is explained in further detail below under reference to the accompanying drawings in which an exemplary embodiment of a pack according to the present invention is depicted.

Figure 3:
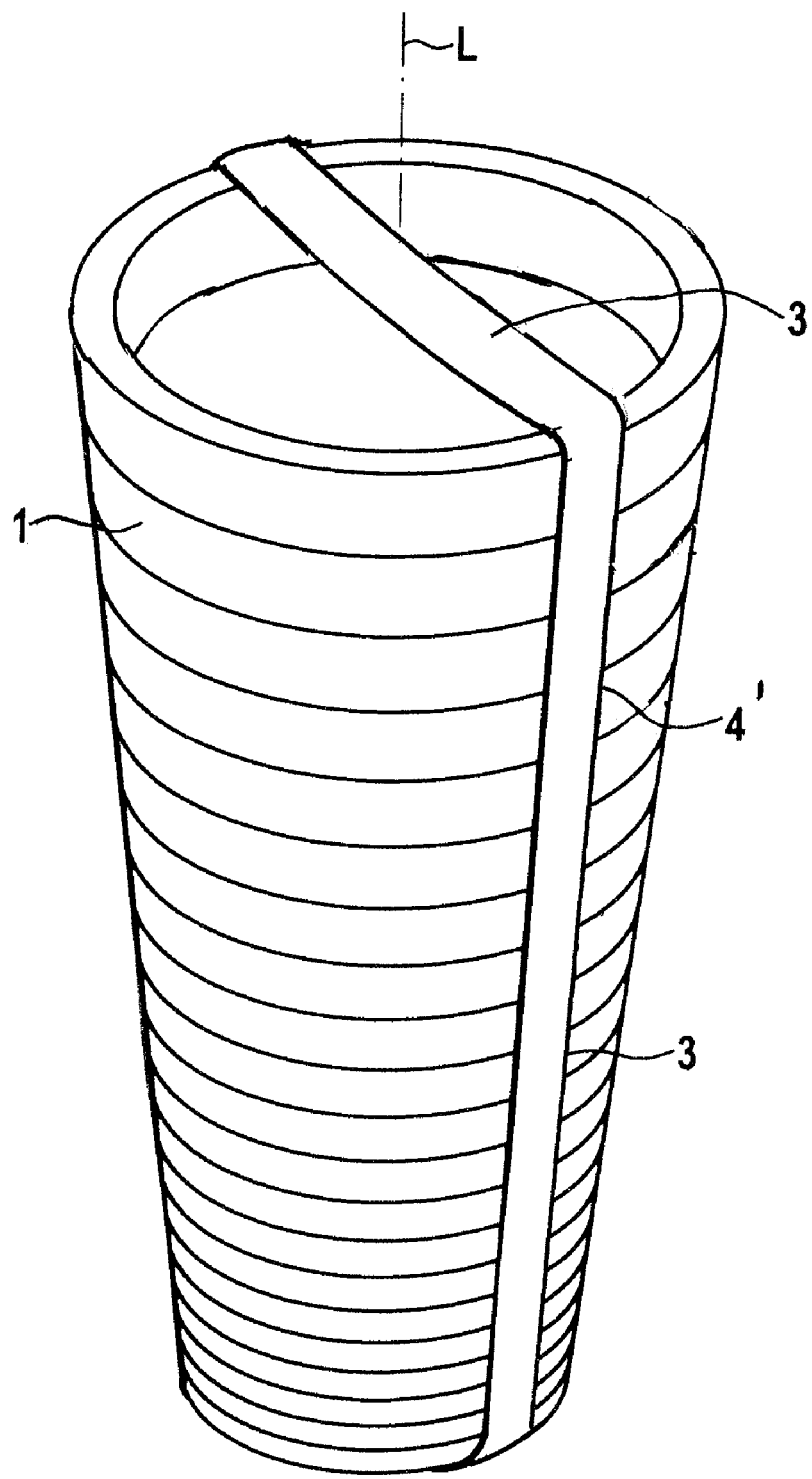
FIG. 3 shows a stack of Petri dishes held together with another exemplary embodiment of a connecting device in a perspective detail drawing.

The exemplary embodiment of the pack according to the present invention illustrated in the drawing and designated overall as 100 comprises a plurality of stacks 2 of Petri dishes 1 that are filled with "pre-poured culture medium," which is not shown in the drawings. Each stack 2 extends in a longitudinal direction L. The Petri dishes 1 belonging to a stack 2 are held together using a detachable connecting device 3. In an embodiment, the connecting device 3 comprises a strap arrangement 4 made from a rubber-elastic material with two strap elements 6, 7 which cross each other twice and at two crossing points (where only the top crossing point 5 is visible). The connecting device 3 can also be formed by a strip material 4' that at least partly surrounds the stack 2 in its longitudinal direction instead of via the strap arrangement 4. Such an embodiment is shown in FIG. 3. The connecting device 3 can easily be released after insertion of the stack 2 into a magazine 8 of a device for laboratory automation, for example, an analysis device, by severing the connecting device 3 with a cutting tool, for example, with a scalpel. In the exemplary embodiment showing strap arrangement 4, this can, for example, be in the region of the upper crossing point 5. The Petri dishes 1 can thereafter be supplied individually from the magazine 8 for use in the analysis device.

In order to shield the stacks of Petri dishes 1 from external influences, and specifically to be able to keep the Petri dishes 1 sterile, the exemplary embodiment of the pack 100 according to the present invention represented in the drawing additionally comprises an outer packaging 9 that is made of a plastic film material. In the exemplary embodiment represented in the drawings, the outer packaging 9 surrounds a stack 2 arranged in four rows of three. In other words, the outer packaging 9 has an interior volume 11 in which the stacks 2 are located. The outer packaging 9 is sealed off from the external environment during the preparation of the pack. It can be opened easily using a cutting tool, for example, a scalpel. A position (not visible in the drawings) can also be provided at which a manual tearing open is facilitated by a material weakness, a scoring, or the like.

The exemplary embodiment of a pack 100 according to the present invention represented in the drawings also comprises a cardboard packaging 10 that accommodates the four times three stacks 2 of Petri dishes 1 including outer packaging 9 and tightly envelops them in the closed state. The cardboard packaging 10 is designed so that it can be non-destructively opened and reclosed. Dampening layers (not shown in the drawings) can be provided between the top and bottom sides of the stacks 2 and the cardboard packaging 10 in their sealed state.

The present invention is not limited to embodiments described herein; reference should be had to the appended claims.

LIST OF REFERENCE NUMERALS

100 Exemplary embodiment
1 Petri dishes
2 Stack
3 Connecting device
4 Strap arrangement
5 Top crossing point
6 Strap element
7 Strap element
8 Magazine
9 Outer packaging
10 Cardboard packaging
11 Interior volume
L Longitudinal direction

What is claimed is:

1. A method of loading a stack of a pack into a magazine of a device for laboratory automation, the method comprising:
   providing a pack consisting of,
      2 to 20 stacks, each of the stacks comprising between 10 and 45 Petri dishes which extends in a longitudinal direction, the Petri dishes either being empty or being filled with a culture medium,
      a connecting device configured to hold each of the stacks together, and
      an outer packaging which is provided as a film packaging, the outer packaging being configured to surround the stacks, to be detachable via a severing process for removing the Petri dishes from each of the stacks, and to be opened either manually or via a cutting tool so as to remove the stacks,
      wherein at least one of,
         the connecting device comprises a strip material which is configured to at least partly surround each of the stacks in the longitudinal direction, the strip material comprising a banner wrap, and
         the connecting device comprises a strap arrangement comprising a rubber-elastic material which is configured to envelop each of the stacks in the longitudinal direction, the strap arrangement being provided either as a single strap element or as two strap elements which are configured to cross over each other and which are connected to each other at two separate crossing points,
      wherein,
         the outer packaging comprises an internal volume that is sterile in an unopened state, and
         the connecting device is arranged inside the outer packaging;
   removing the outer packaging of the pack;
   inserting one of the stacks of the pack into the magazine of the device for laboratory automation; and
   releasing the connecting device which is configured to hold the inserted stack together.

2. The method as recited in claim 1, wherein,
   the at least one stack comprises 6 or 12 stacks, and
   6 of the stacks are arranged in 2 rows of 3 stacks each in the outer packaging, or
   12 stacks are arranged in 4 rows of 3 stacks each in the outer packaging.

3. The method as recited in claim 1, further comprising:
   a cardboard packaging configured to hold and at least partly surround the outer packaging.

4. The method as recited in claim 3, wherein the cardboard packaging is further configured be opened and reclosed without damage.

5. The method as recited in claim 3, wherein,
   the cardboard packaging is further configured for the tightly enveloping inclusion of 4 rows of 3 stacks each,
   each of the stacks comprises 10 to 20 Petri dishes, and
   the cardboard packaging is surrounded by the outer packaging.

6. The method as recited in claim 3, further comprising;
   a dampening layer arranged between a bottom side of the at least one stack and the cardboard packaging.

7. The method as recited in claim 6, wherein the dampening layer is further arranged between a top side of the at least one stack and the cardboard packaging.

8. The method as recited in claim 6, wherein the dampening layer is an air pillow.

9. A method of loading a stack into a magazine of a device for laboratory automation, the method consisting of:
   providing a pack consisting of,
      2 to 20 stacks, each of the stacks comprising between 10 and 45 Petri dishes which extend in a longitudinal direction, the Petri dishes either being empty or being filled with a culture medium,
      a connecting device configured to hold each of the stacks together, and
      an outer packaging which is provided as a film packaging, the outer packaging being configured to surround the stacks, to be detachable via a severing process for removing the Petri dishes from each of the stacks, and to be opened either manually or via a cutting tool so as to remove the stacks,
      wherein at least one of,
         the connecting device comprises a strip material which is configured to at least partly surround each of the stacks in the longitudinal direction, the strip material comprising a banner wrap, and
         the connecting device comprises a strap arrangement comprising a rubber-elastic material which is configured to envelop each of the stacks in the longitudinal direction, the strap arrangement being provided either as a single strap element or as two strap elements which are configured to cross over each other and which are connected to each other at two separate crossing points,
      wherein,
         the outer packaging comprises an internal volume that is sterile in an unopened state, and
         the connecting device is arranged inside the outer packaging;
   removing the outer packaging of the pack;
   inserting one of the stacks of the pack into the magazine of the device for laboratory automation; and
   releasing the connecting device which is configured to hold the inserted stack together.

10. A method of using a pack in a device for laboratory automation, the method comprising:
   providing a pack consisting of,
      2 to 20 stacks, each of the stacks comprising between 10 and 45 Petri dishes which extends in a longitudinal direction, the Petri dishes either being empty or being filled with a culture medium, a connecting device configured to hold each of the stacks together, and an outer packaging which is provided as a film packaging, the outer packaging being configured to surround the stacks, to be detachable via a severing process for removing the Petri dishes from each of the stacks, and to be opened either manually or via a cutting tool so as to remove the stacks, wherein at least one of, the connecting device comprises a strip material which is configured to at least partly surround each of the stacks in the longitudinal direction, the strip material comprising a banner wrap, and the connecting device comprises a strap arrangement comprising a rubber-elastic material which is configured to envelop each of the stacks in the longitudinal direction, the strap arrangement being provided either as a single strap element or as two strap elements which are configured to cross over each other and which are connected to each other at two separate crossing points, wherein, the outer packaging comprises an internal volume that is sterile in an unopened state, and the connecting device is arranged inside the outer packaging;

removing the outer packaging of the pack;

inserting one of the stacks of the pack into a magazine of the device for laboratory automation;

releasing the connecting device which is configured to hold the inserted stack together; and using the pack in the device for laboratory automation.

11. The method of using as recited in claim 10, wherein the releasing of the connecting device is performed via a severing process.

\* \* \* \* \*